United States Patent [19]

Jain

[11] 4,426,323

[45] * Jan. 17, 1984

[54] SELECTED RECOVERY OF PROTEINS FROM FERMENTATION BROTHS

[75] Inventor: Surendar Jain, Watertown, Mass.

[73] Assignee: Ionics, Incorporated, Watertown, Mass.

[*] Notice: The portion of the term of this patent subsequent to Mar. 30, 1999 has been disclaimed.

[21] Appl. No.: 271,069

[22] Filed: Jun. 8, 1981

Related U.S. Application Data

[63] Continuation-in-part of Ser. No. 256,264, Apr. 21, 1981, which is a continuation-in-part of Ser. No. 111,144, Jan. 10, 1980, Pat. No. 4,276,140.

[51] Int. Cl.$^3$ .......................... A23J 1/06; A23K 37/04; C07G 7/00; G12P 21/00
[52] U.S. Cl. ............................. 260/112 R; 204/180 P; 204/180 R; 204/301; 424/85; 424/177; 435/68; 435/811
[58] Field of Search ...................... 260/112 R; 424/85; 425/68, 811

[56] References Cited

U.S. PATENT DOCUMENTS

| | | | |
|---|---|---|---|
| 3,414,651 | 12/1968 | Fantes | 424/85 |
| 3,975,344 | 8/1976 | Schwartz | 424/85 |
| 4,168,261 | 9/1979 | Edy | 424/85 X |
| 4,257,938 | 3/1981 | Hosoi et al. | 260/112 R |
| 4,276,140 | 6/1981 | Jain | 260/112 R X |
| 4,296,025 | 10/1981 | Sugimoto | 435/68 X |
| 4,321,192 | 3/1982 | Jain | 260/112 R X |
| 4,322,275 | 3/1982 | Jain | 260/112 R X |

Primary Examiner—Howard E. Schain
Attorney, Agent, or Firm—Norman E. Saliba

[57] ABSTRACT

A process is described for the selective recovery and/or concentration of a protein or a class of proteins from fermentation broth employing a combination of desalting and pH adjustment thereby causing the initial precipitation of unwanted proteins, again subjecting the resulting supernatant to another set of pH adjustment and desalting to cause the protein of interest to precipitate thereby obtaining a highly enriched fraction of the selected protein. Such a process will find use in the specific recovery of genetically engineered proteins from fermentation broths, e.g. interferon, insulin, growth hormone, etc.

13 Claims, No Drawings

SELECTED RECOVERY OF PROTEINS FROM FERMENTATION BROTHS

FIELD OF INVENTION

This application is a continuation-in-part of application Ser. No. 256,264 filed Apr. 21, 1981 which is in turn a continuation-in-part of Ser. No. 111,144 filed Jan. 10, 1980 now U.S. Pat. No. 4,276,140. This invention relates to the removal and separation of impurities from a fermentation broth and thereafter the precipitation and concentration of a protein of interest from the remaining fermentation broth supernatant.

BACKGROUND AND PRIOR ART

The term fermentation refers to the aerobic and/or anaerobic metabolic activities of micro-organisms in which specific chemical changes are brought about in an organic substrate or raw material. From the microbiology standpoint the meaning includes almost any process mediated by or involving a micro-organism in which a product of value accrues. [Ref. Casida, L. E. Industrial Microbiology, John Wiley & Sons, NY (1968)]. Intensive research has yielded know-how for selecting the most efficient strains from the vast number of natural or genetically engineered organism thereby optimising the biochemical reactions of choice. Microorganisms (bacteria, fungi, yeast) multiply extremely fast on nutritive substrates of suitable composition under closely defined conditions of pH, temperature, concentration of nutrients, etc. The equipment in which such biochemical reactions are carried out are called fermenters. The desired product is normally a compound formed during the primary or secondary metabolic processes and is usually present in the fermentation broth mixture in a very low concentration. The mixture normally comprises a substrate or raw material, micro-organisms, nutrients, additives, by-products, etc. The techniques employed for separation of the impurities and recovery of the desired product(s) are very extensive and may consist of sedimentation, filtration or contrifugation, extraction, precipitation, adsorption, elution, ion exchange, affinity chromotography, etc. [Gerstenberg, H.; Sittig, Wolfgang; Zepf, Karheinz. Ger. Chem. Eng. 3 (1980) 313–3277.]

DETAILED DESCRIPTION

Different kinds of biological cells can make various proteins, following instructions encoded in the DNA of their genes. Recent advances in molecular biology now make it possible to alter these instructions in bacterial cells, thereby designing bacteria that can synthesize non-bacterial proteins. These bacteria are "recombinants" and contain along with their own genes, part or all of a gene from a human or other animal cell. If the inserted gene is one for a protein with an important biomedical application, a culture of the recombinant bacteria, which can be grown easily and at low cost will serve as an efficient factory for production of that protein. (Gilbert, Walter; Villa-Kamaroff, Lydia; "Useful Proteins from Recombinant Bacteria", Scientific American, April 1980). E-coli is the most commonly used bacteria cell but recently other bacteria cells and yeast have also been used to genetically engineer proteins (Chem. Marketing Reports, Mar. 2, 1981).

These techniques have found special applications in producing interferons which are a family of low molecular weight glycoproteins produced by vertebrate cells in response to a variety of stimuli, e.g. viruses, microbes, nucleic acids, etc. The interferons are not per se directly responsible for antiviral activity but induce the synthesis of specific proteins in host cells which are responsible for the inhibitory effect. The role of interferons in exploring the therapeutic potential was severely hampered by the limited supply of material available and the high cost ($20,000–30,000) for treating one patient. With genetically engineered methods, larger quantities of the protein will become available at a reduced cost.

Another protein capable of being produced by genetic engineering is insulin which is used in the treatment of diabetes. Until recently this protein was produced exclusively from bovine or procine pancreas by extraction with acid or alkaline solutions of alcohols or acetone. Purification of the protein was achieved by fractional precipitation of the extract with alcohol, by isoelectric precipitation, by salting out, by adsorption, by separation of the hormone as an insoluble salt etc., or by combining several of these methods or steps in a suitable sequence. [Kirk Othmer, Encyclopedia of Chemical Technology, 2nd Edition, Vol. 11, p. 842, John Wiley & Sons, N.Y. (1965)]. With the recombinant DNA techniques there is the potential for producing a more specific insulin hormone for humans thereby minimizing the side effects.

The genetically engineered strains of bacteria, yeast, etc., are made to multiply in a protein of choice by use of a fermentation process under carefully controlled conditions of temperature, pH, nature of nutrients, salts, etc. At the conclusion of the fermentation process, the broth is clarified by separating the suspended cells and other particulate matter. The separation of the protein of choice can then be undertaken by a series of steps as outlined hereinafter.

This application discloses an invention which is an improvement over that disclosed in my co-pending application Ser. No. 256,264 filed Apr. 21, 1981 which discloses a process for desalting a plasma protein solution by dialysis along with pH adjustment for the purpose of separating and recovering the antihemophilic factor (AHF). In the present invention, the recovery of a selected protein such as interferon from a fermentation broth is made possible by a novel combination of salt removal steps and/or pH adjustments of the broth. The collective isoelectric point of the impurities can be determined by desalting a broth to various salt levels with adjustment of the pH to various values to thus determine where the maximum removal of impurities occurs with the minimum loss of the product of interest. Likewise after the initial removal of impurities, the product of interest can be precipitated out in a relatively pure form by a combination of desalting and adjustment of the pH to the pI of the product. Thus this present method can serve as a powerful tool in the concentration and/or purification of products from fermentation broths and can replace many of the presently practised methods.

This invention involves the use of a continuous flow system whereby the salt concentration of the protein solution is decreased by the removal of salts (ions) through known semi-permeable membrane systems such as by electrodialysis, dialysis, and/or ultrafiltration systems. Electrodialysis (ED) equipment and methods of operation are more fully described in U.S. Pat. Nos. 2,848,403; 2,863,813; 3,003,940; 3,341,441; 4,115,225 and others. An electrodialysis stack normally comprises one or more pairs of a salt concentrating and salt diluting chamber separated by alternating anion and cation selective membranes. One or more selective membranes may at times be replaced by neutral or non-selective membranes. The chambers are located between an anode and a cathode electrode. An electrolyte solution is preferably passed through the cathode and anode chambers to conduct current across the concentrating and the diluting chambers. Usually a concentrating chamber is located so as to isolate the electrode solutions from the product or diluting chamber. The ion selective membraes are selected depending on the solution under treatment and the liquid flow rates through the stack. The applied current is carefully regulated to obtain the desired results. The protein solution is passed into and through the diluting chambers and on impressing a direct current across the electrodes, the salt or ionic content of the protein solution is reduced due to the passage of salt through the membranes into the adjacent concentrating chambers. The concentrating chambers may be primed initially with a small amount of NaCl electrolyte solution. The resulting desalted protein solution is collected from the diluting chambers and treated to separate and remove one or more of the desired proteins.

Dialysis is another membrane separation process useable in the present invention where the driving force is a gradient in chemical potential, e.g. a gradient in concentration or activity of the solutes across the membrane separating the two solutions. The membrane employed is permeable to water and low molecular weight solutes. The solute diffuses through the membrane until the concentration gradient is negligible on both sides of the membrane. Thus dialysis can be quite an efficient process in situations where high concentration gradients are involved. The main application of the prior art dialysis is the kidney dialysis field where low molecular weight solutes, like urea and some salts, are removed from blood. Such hemodialysis systems are fully described in U.S. Pat. No. 4,192,748; 4,191,646; 4,213,859; 3,960,730, and others. These patents, however, are concerned merely with reducing the salt content and low molecular weight proteins like urea, creatinine, B-12, etc. rather than using the dialysis process in a complex scheme of fractionating a fermentation broth for the recovery of a specific protein component like interferon.

This technique of fractionating proteins by desalting (which may be accomplished by membrane processes such as electrodialysis, dialysis, etc.) is very useful in the recovery and/or purification of genetically engineered proteins produced by a fermentation process and can be efficaciously incorporated in the various steps for recovery of the protein of choice. Generally the concentration of the selected protein of interest in the fermentation broth is very low since the impurities therein represent a major part of the total proteins in the mixture. It is therefore advantageous to either precipitate out the impurities by the judicious choice of desalting and/or pH adjustment (either a single step of desalting and/or pH adjustment or by several desalting and/or pH adjustment steps) or the protein of choice may be separated out instead by a combination of desalting and pH adjustment. Alternatively the removal of the impurities and separation of the protein of choice may be accomplished in tandem by single or multiple desalting and/or pH adjustment steps. Improved precipitation (either of the impurities or the protein of choice) is facilitated when in addition to desalting the pH is brought close to the collective pI (isoelectric point) of the impurities or of the individual pI of the protein of choice. The above mentioned pH adjustments may be accomplished before, during or after the desalting step which is preferably accomplished by the dialysis or electrodialysis technique. The pH adjustment may be made by the direct addition of acid or alkali to the protein mixture or its supernatant and/or by controlling the pH of the adjacent non-protein stream.

A specific example of the utilization of this desalting and/or pH adjustment combination is in the purification and recovery of interferon from fermentation broth or its derived fractions. The broth is desalted (by membrane electrodialysis or dialysis) to remove between about 60-85% of its original salt content, the pH of the protein mixture is brought into the range of between 4 to 5 (preferably 4.5) to thus maximize the removal of impurities by the formation of a turbid phase containing mostly impurities.

After separation of the turbid impurities, the pH of the remaining supernatant may optionally be adjusted to between about 5-8 and the said process of desalting again carried out until the mixture is about 90% or more desalted (based on the original salt content). The pH will normally decrease as a result of the desalting (by ED or dialysis) or it may be need to be adjusted by the above described manner (e.g. by controlling the pH of the adjacent stream) in order to bring the pH of the supernatant protein mixture within the pH of interferon (5–6) thereby facilitating its precipitation and purification. Subsequently this precipitation is separated and resuspended to generate a more concentrated form of interferon which may then be used or if required sent to additional purification.

Although this example is described with two separate desalting and three separate pH adjustment steps (one to remove the initial impurities, a second optional pH adjustment step to readjust the pH to between 5-8, and the third step to recover the protein of choice, i.e., interferon), several other combinations of desalting and/or pH adjustments can be devised by those skilled in the art to further refine this process. The above described example or the description of the number of desalting/pH adjustment steps or their order of use should not be construed as a limitation of this process. Further, the process of the present invention can also be used in conjunction with non-genetically engineered processes.

The isoelectric point is defined by Hackh's Chemical Dictionary, Third Edition, 1944, The Blakiston Company, Edited by J. Grant, page 454, as the point of electric neutrality or zero potential, meaning the pH value at which a substance such as interferon is neutral.

The above described techniques thus have the potential of simplifying and greatly reducing the number of steps required in the purification of natural and genetically engineered proteins.

While the invention has been herein shown and described in what is presently conceived to be the most practical and preferred embodiment thereof it will be apparent to those of ordinary skill in the art that many modifications may be made thereof within the scope of the invention, which scope is to be accorded the broadest interpretation of the appended claims so as to encompass all equivalent assemblies and methods.

The embodiments of this invention in which an exclusive property or privilege is claimed are defined as follows:

1. A process for separating and recovering a selected protein or selected group of proteins from a fermentation broth containing a mixture of selected and non-selected proteins comprising the steps of:
   (a) removing when present substantially all initial turbidity from said broth;
   (b) subsequently passing said broth into and out of a membrane desalting apparatus in contact with one surface of one or more semi-permeable membranes, said membrane separating said broth stream from an adjacent salt receiving stream thereby causing a decrease in the salt concentration of said broth;
   (c) said broth being adjusted in pH to within substantially the collective isoelectric point range of the non-selected protein sufficient to cause the formation of a first turbid phase containing essentially the said non-selected proteins and a first liquid phase enriched in the said selected protein;
   (d) subsequently removing substantially all of said first formed turbid phase;
   (e) passing the remaining first liquid phase into and out of said desalting apparatus to further decrease the salt concentration;
   (f) adjusting the pH to within the isoelectric point of the selected protein of interest thereby forming a second turbid phase enriched in the said selected protein of interest;
   (g) and separating the said second turbid phase for subsequent resuspension or purification.

2. The process of claim 1 wherein the pH of the remaining first liquid phase is adjusted to between about 5–8 prior to further desalting in step (e).

3. A process for separating and recovering interferon from a fermentation broth containing a mixture of interferon and other proteins comprising the steps of:
   (a) removing when present substantially all initial turbidity from said broth;
   (b) subsequently passing said broth into and out of a membrane desalting apparatus in contact with one surface of one or more semi-permeable membranes, said membrane separating said broth stream from an adjacent salt receiving stream thereby causing the removal of between about 60–80% of the original salt concentration of said broth;
   (c) said broth being adjusted in pH to between about 4–5 to cause the formation of a first turbid phase containing essentially the said other proteins and a first liquid phase enriched in said interferon;
   (d) subsequently removing substantially all of said first formed turbid phase;
   (e) passing said remaining first liquid phase into and out of said desalting apparatus causing the further removal of at least about 90% of the original salt concentration of said broth;
   (f) adjusting the pH to within the isoelectric point of interferon thereby forming a second turbid phase enriched in said interferon;
   (g) and separating the said interferon enriched turbid phase for subsequent resuspension or purification.

4. The process of claim 3 wherein the pH of the remaining first liquid phase is adjusted to substantially neutral prior to further desalting in step (e).

5. A process of claim 1 wherein the membrane desalting apparatus is a dialyzer.

6. A process of claim 1 wherein the membrane desalting apparatus is an electrodialyzer.

7. A process of claim 1 wherein the pH adjustment in step (c) is made prior to said desalting of step (b).

8. A process of claim 1 wherein the pH adjustment in step (c) is made simultaneously with the said desalting of step (b).

9. A process of claim 1 wherein the pH adjustment in step (c) is made after the said desalting of step (b).

10. A process of claim 1 wherein the pH adjustment in step (c) is accomplished by controlling the pH of the said adjacent salt receiving stream of the membrane desalting apparatus.

11. A process of claim 1 wherein the pH adjustment in step (f) is made simultaneously with the said desalting of step (e).

12. A process of claim 1 wherein the pH adjustment in step (f) is made after the said desalting of step (e).

13. A process of claim 1 wherein the pH adjustment in step (f) is accomplished by controlling the pH of the said adjacent salt receiving stream of the membrane desalting apparatus.

* * * * *